(12) United States Patent
Wolfe et al.

(10) Patent No.: US 10,492,711 B2
(45) Date of Patent: Dec. 3, 2019

(54) HANDHELD PORTABLE IMPULSE OSCILLOMETER

(71) Applicants: Michael W. Wolfe, Pine Mountain, GA (US); Katherine C. Wolfe, Pine Mountain, GA (US)

(72) Inventors: Michael W. Wolfe, Pine Mountain, GA (US); Katherine C. Wolfe, Pine Mountain, GA (US)

( * ) Notice: Subject to any disclaimer, the term of this patent is extended or adjusted under 35 U.S.C. 154(b) by 589 days.

(21) Appl. No.: 15/168,152

(22) Filed: May 30, 2016

(65) Prior Publication Data
US 2016/0345860 A1 Dec. 1, 2016

Related U.S. Application Data

(60) Provisional application No. 62/168,854, filed on May 31, 2015.

(51) Int. Cl.
| | |
|---|---|
| *A61B 5/085* | (2006.01) |
| *A61B 5/097* | (2006.01) |
| *A61B 5/00* | (2006.01) |
| *G16H 40/67* | (2018.01) |

(52) U.S. Cl.
CPC ............ *A61B 5/085* (2013.01); *A61B 5/0022* (2013.01); *A61B 5/097* (2013.01); *A61B 5/742* (2013.01); *G16H 40/67* (2018.01); *A61B 2560/0214* (2013.01); *A61B 2560/0252* (2013.01); *A61B 2560/0257* (2013.01); *A61B 2560/0425* (2013.01); *A61B 2560/0431* (2013.01); *A61B 2562/0247* (2013.01)

(58) Field of Classification Search
USPC ........................................................ 600/533
See application file for complete search history.

(56) References Cited

U.S. PATENT DOCUMENTS

| | | | | |
|---|---|---|---|---|
| 5,856,745 | A * | 1/1999 | Morgan | F15B 15/2869 324/633 |
| 6,237,748 | B1 * | 5/2001 | Kroger | B06B 1/045 198/750.5 |
| 6,244,865 | B1 * | 6/2001 | Nelson | A61B 5/097 128/205.29 |
| 7,325,545 | B2 * | 2/2008 | Dellaca' | A61B 5/085 128/200.24 |

(Continued)

*Primary Examiner* — Jason C Olson (57) ABSTRACT

A multitude of clinical research studies have validated the superiority of impulse oscillometry (IOS) over spirometry because it is far more sensitive in the detection of pulmonary diseases and since it is effort-independent, it can be successfully used in children as young as six-months old. By miniaturizing the IOS to be a hand-held and portable device, the present invention takes IOS technology out of the exclusive environments of the research lab and specialty Pulmonology office. Also by advancing the technology, the manufacturing cost is greatly reduced thereby making the device affordable and available to the average primary care physician for use in their office. In addition, as the present invention becomes available as a home-use device, it will significantly improve the home management of complex respiratory diseases, i.e., Asthma and COPD. The present invention, being a miniaturized and electromagnetically piston-driven IOS, is truly unique in its concept and technology.

5 Claims, 6 Drawing Sheets

Airflow Diagram of Double Tube Design (56) References Cited

U.S. PATENT DOCUMENTS

| | | | | |
|---|---|---|---|---|
| 8,100,836 B2* | 1/2012 | Diong | .................. | G09B 23/288 |
| | | | | 600/529 |
| 8,449,474 B2* | 5/2013 | Schuessler | ............. | A61B 5/085 |
| | | | | 417/415 |
| 8,641,637 B2* | 2/2014 | Sly | ........................... | A61B 5/08 |
| | | | | 600/529 |
| 2007/0161918 A1* | 7/2007 | Ganshorn | ............... | A61B 5/085 |
| | | | | 600/533 |
| 2009/0129955 A1* | 5/2009 | Schubert | ............... | F04B 35/045 |
| | | | | 417/417 |
| 2010/0011954 A1* | 1/2010 | Reininger | ........... | F15B 15/2869 |
| | | | | 92/5 R |
| 2011/0092840 A1* | 4/2011 | Forbes | .................. | A61B 5/0876 |
| | | | | 600/538 |
| 2012/0277615 A1* | 11/2012 | Coifman | .............. | A61B 5/0876 |
| | | | | 600/538 |
| 2013/0245980 A1* | 9/2013 | Forbes | .................. | A61B 5/0876 |
| | | | | 702/86 |
| 2013/0287611 A1* | 10/2013 | Schmidt | .................. | F04B 25/02 |
| | | | | 417/443 |
| 2015/0126888 A1* | 5/2015 | Patel | ...................... | A61B 5/087 |
| | | | | 600/538 |
| 2016/0121062 A1* | 5/2016 | Davenport | ............. | A61B 5/097 |
| | | | | 601/47 |
| 2017/0270260 A1* | 9/2017 | Shetty | .................. | A61B 5/6898 |

* cited by examiner

HANDHELD PORTABLE IMPULSE OSCILLOMETER

The present device is a miniaturized handheld portable impulse oscillometer (IOS) device designed to assess and analyze lung functions for the diagnosis and treatment of the full range of pulmonary diseases. IOS is an accepted pulmonary functions test (PFT) and is widely used in pulmonary medicine. The present device is a Class II medical device.

CROSS-REFERENCE TO RELATED APPLICATIONS (1) *Impulse Oscillometry: Interpretation and Practical Application*, Chest Journal, September 2014, Volume 146, No. 3, Dr. Burton Lesnick, et al.
(2) 2004 *Global Burden of Asthma Report*, Global Initiative for Asthma (GINA), Sponsored by the National Heart, Lung, and Blood Institute, NIH and the World Health Organization (WHO).
(3) (2013). "Asthma's Impact on the Nation (2012)." 2014, from http://www.cdc.gov/asthma/impacts_nation/default.htm?s_cid=tw_DrCP274,
(4) Erika G Meraz, Homer Nazeran, Carlos D Ramos, Pat Nava, Bill Diong and Michael D Goldman, *Analysis of Impulse Oscillometric Measures of Lung Function and Respiratory System Model Parameters In Small Airway-Impaired and Healthy Children Over a 2-Year Period*, U.S. National Institute of Environmental Health Sciences (NIEHS—S11 ES013339—Pilot 1 PI: HN), NIH.
(5) 2012; *Peripheral Airway Impairment Measured by Oscillometry Predicts Loss of Asthma Control in Children*. Yxin Shi, M S, Anna S. Aledia, B S, Stanley P. Galant, M D, Steven C. Goerge, M D, PhD, Jun. 6, 2012 NIH www.jacionline.org article S0091/6749%2901544-8/full text.
(6) PMCID: PMC381359 NIHMSID: NIHMS 509309— *Invasive Testing of Lung Function and Inflammation in Pediatric Patients With Acute Asthma Exacerbations*. Ann Allergy Asthma Immunol. Author manuscript; available in PMC Jul. 23, 2012. Published in final edited form as: Ann Allergy Asthma Immunol. March 2011; 106(3): 191-199. Published online Jan. 6, 2011. doi: 10.1016/j.anai.2010.11.011
(7) 2012 NIH sponsored study: *Impulse Oscillometry in the Evaluation of the Airways in Children*, Hirsh D. Komarow, MD., Laboratory of Infectious Diseases, NIAID, NIH.
(8) Lappas, A. ( ) Forced oscillations in applied respiratory physiology. Pneumon, 26.
(9) Carefusion. Technical Specifications for Impulse Oscillometry. Available at: http://www.carefusion.com/pdf/Respiratory/Pulmonary_Function_Testing/MasterScreen_IOS_ Specifications. Accessed Feb. 13, 2014.
(10) Abou-atme Y S, Chedid N, Melis M, Zawawi K H. Clinical measurement of normal maximum mouth opening in children. Cranio. 2008; 26(3):191-6.
(11) Fang Y, Ma G, Lou N, Liao W, Wang D. Preoperative Maximal Oxygen Uptake and Exercise-induced Changes in Pulse Oximetry Predict Early Postoperative Respiratory Complications in Lung Cancer Patients. Scand J Surg. 2014
(12) Behrakis P, Lappas A, Tzortzi A. Forced Oscillations in Applied Respiratory Physiology. JAMA. December 2013; No 4 Vol 26:327-345.
(13) Non-Heated Pneumotachometer. (2014, Jan. 1). Non-Heated Pneumotachometer. Retrieved Apr. 1, 2014, from http://www.harvardapparatus.com/webapp/wcs/stores/servlet/haisku3_10001_11051_41149-1_HAI_ProductDetail_n_37840_37841_37844
(14) Rothenberg, M. ( ). Measurement of Airflow in Speech. Journal of Speech and Hearing Research, 20, 155-176.

STATEMENT REGARDING FEDERALLY SPONSORED RESEARCH OR DEVELOPMENT

Not Applicable

REFERENCE TO A "SEQUENCE LISTING"

Not Applicable

BACKGROUND OF THE INVENTION (1) Field of the Invention
Classifications
U.S. Classification 600/538, 417/415
International Classification F041335/04, A61B5/085, A61B5/087
Cooperative Classification A61B5/097
(2) Description of Related Art

| Cited Patents | Filing Date | Publication Date | Applicant | Title |
|---|---|---|---|---|
| U.S. Pat. No. 8,449,474 B2 | Jun. 28, 2006 | May 28, 2013 | Scireq Sc Res Eq | Self-actuated cylinder and Oscillation spirometer |
| U.S. Pat. No. 5,856,745 | Feb. 14, 1997 | Jan. 5, 1999 | Caterpillar Inc. | Hydraulic cylinder end Member arrangement for a piston position sensing system |
| U.S. Pat. No. 8,641,637 B2 | Feb. 4, 2013 | | Sly | Method of measuring an acoustic impedance of a respiratory system . . . |
| U.S. Pat. No. 5,318,038 | Jun. 7, 1994 | | Jackson | Infant respiratory impedance measuring apparatus . . . |
| EP 0616792 B1 | Jun. 3, 1998 | | Dipl-Ing | Oscillometric determination of the airway impedance, . . . |
| U.S. Pat. No. 8,100,836 | Jan. 24, 2012 | | Diong | Augmented RIC model of respiratory systems . . . |
| U.S. Pat. No. 7,325,545 | Feb. 5, 2008 | | Dellaca | System & method of automatic detection of the expiratory flow limitation. |
| U.S. Pat. No. 7,402,139 | Jul. 22, 2008 | | Ganshorn | Appliance for the oscillometric analysis of the impedance of the respiratory tract. |

BRIEF SUMMARY OF THE INVENTION

The current impulse oscillometers on the market are large medical devices, are very expensive, and are mainly found in specialized PFT clinics or research laboratories. The present device is handheld, portable, low cost, and is intended for the primary care provider and for home use by the patient.

BRIEF DESCRIPTION OF DRAWINGS (1) Piston Detail—Provides specifics of the piston cylinder and the relation of the ring-shaped electromagnets with drive the piston.

(2) Airflow Diagram—Describes the air impulse tube which houses the piston cylinder and is surrounding by the tidal airflow tube. Arrows illustrate laminar air flow.

(3) Lateral Resection—Illustrates the positioning of the double tube (air impulse tube and tidal breathing tube) within the overall handheld portable impulse oscillometer.

(4) Front Resection—Shows the double tube from the front of the device.

(5) Carrying Case—Case shows the positioning of the device cradled for transportation, relation with the dryer unit, and the location of the data screen and pullout key board.

(6) Dryer Unit—Blows warmed air though the double tube after use to remove any humidity present.

DETAILED DESCRIPTION OF THE INVENTION

Impulse oscillometry (IOS) measures the amount of inflammation occurring within the central airways and within the peripheral airways of the lungs including the alveoli or small air sacs located at the very ends of the bronchial tubes. By emitting low frequency air impulses into the lungs, the air impulses travel throughout the small airways, and this is the main location where inflammation occurs. While spirometry depends on the patient taking an extreme deep breath and then forcibly exhaling as hard as they can to measure total lung volume, the action only measures complications within the central airways. Spirometry is considered a patient dependent test because the success of the test depends on how hard the patient is willing or is able to participate. Impulse oscillometry is termed a patient independent test because all the patient does is breath normally (tidal breathing) through the device. The gentle low frequency air impulses travel throughout the patient's central and peripheral airways measuring the amount of swelling or resistance as the impulse penetrates the lungs, and then measures the amount of elasticity, or reactance, as the impulses bounce back to the IOS.

Figure 2:
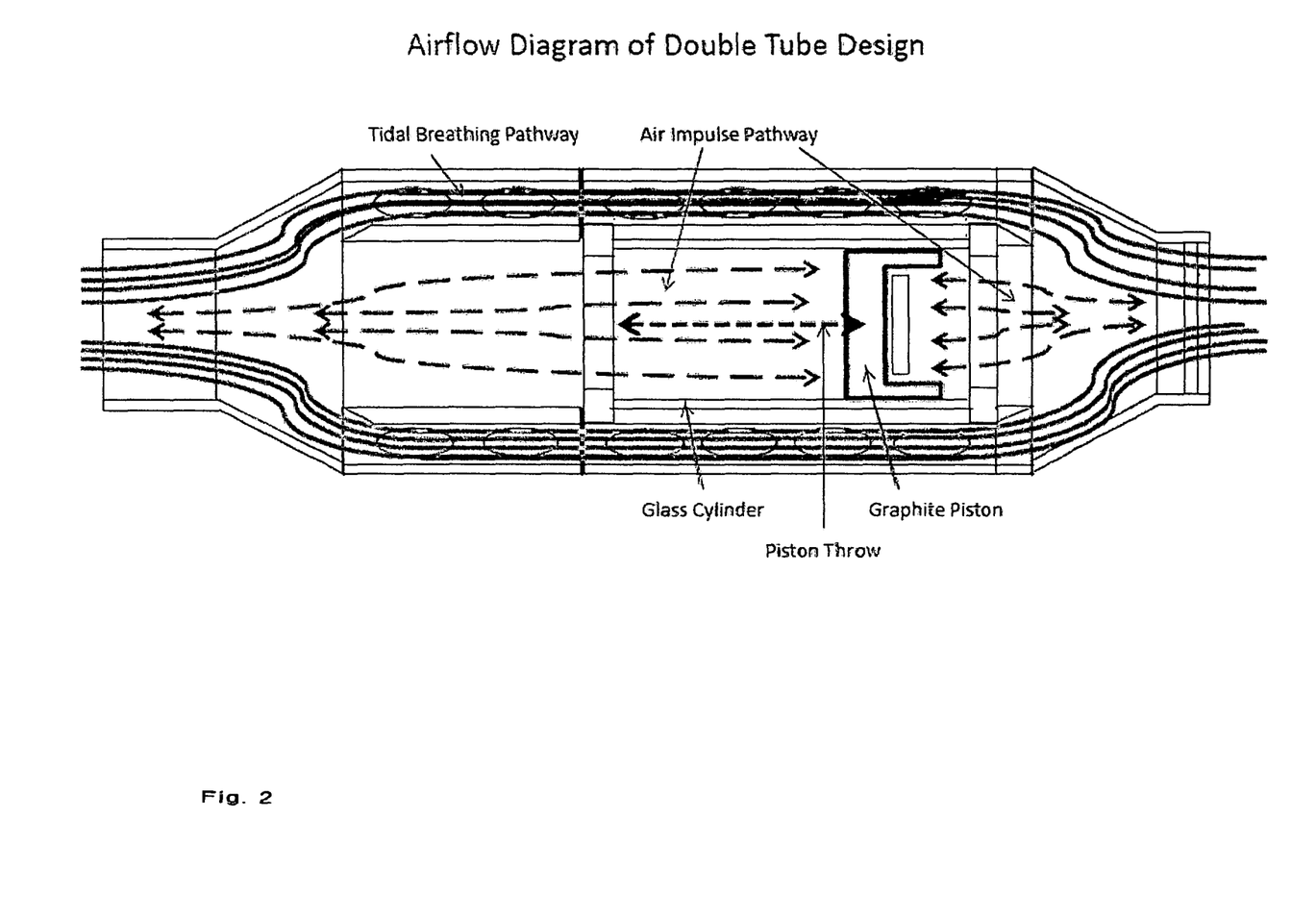
Figure 3:
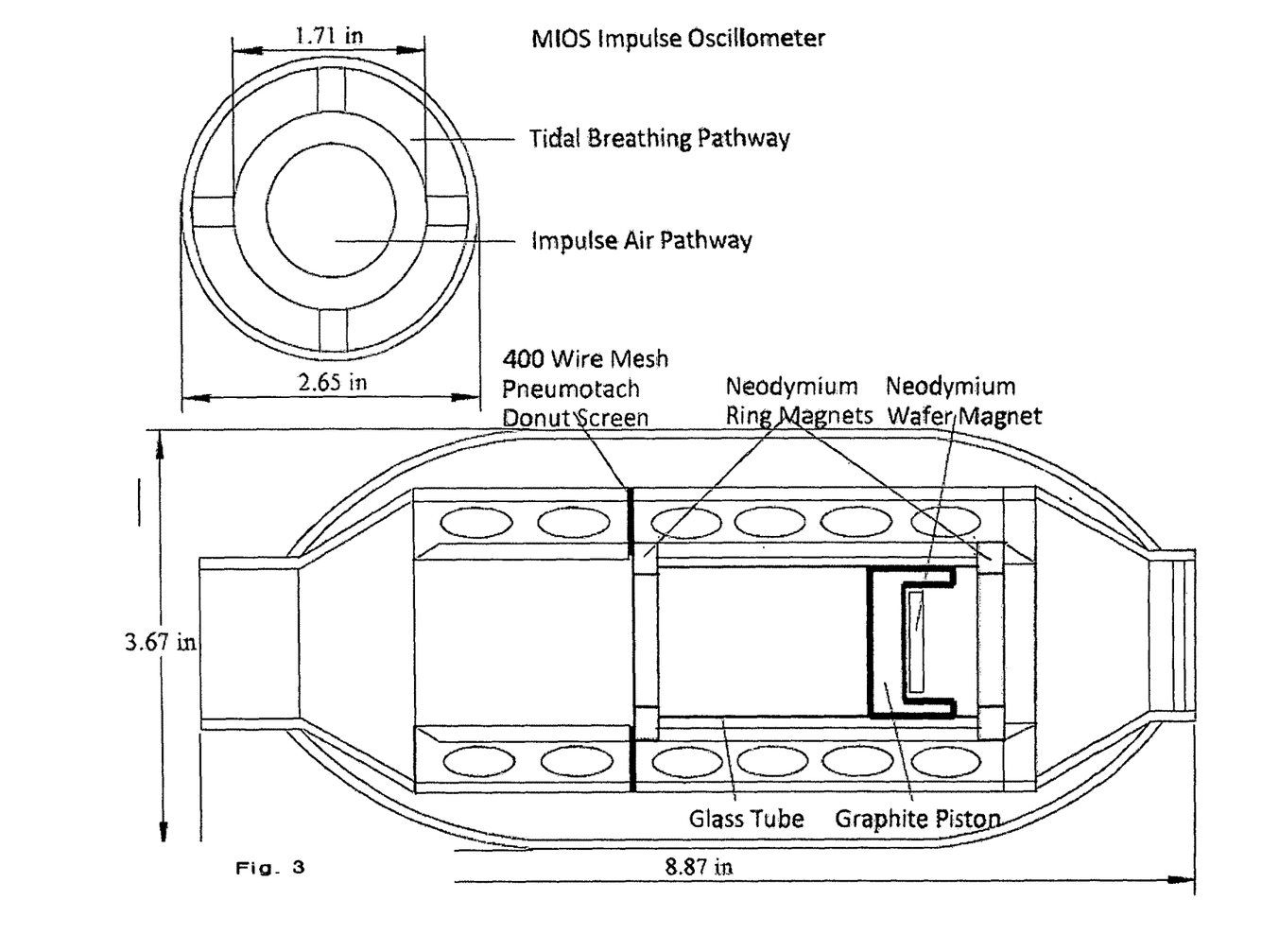
Figure 4:
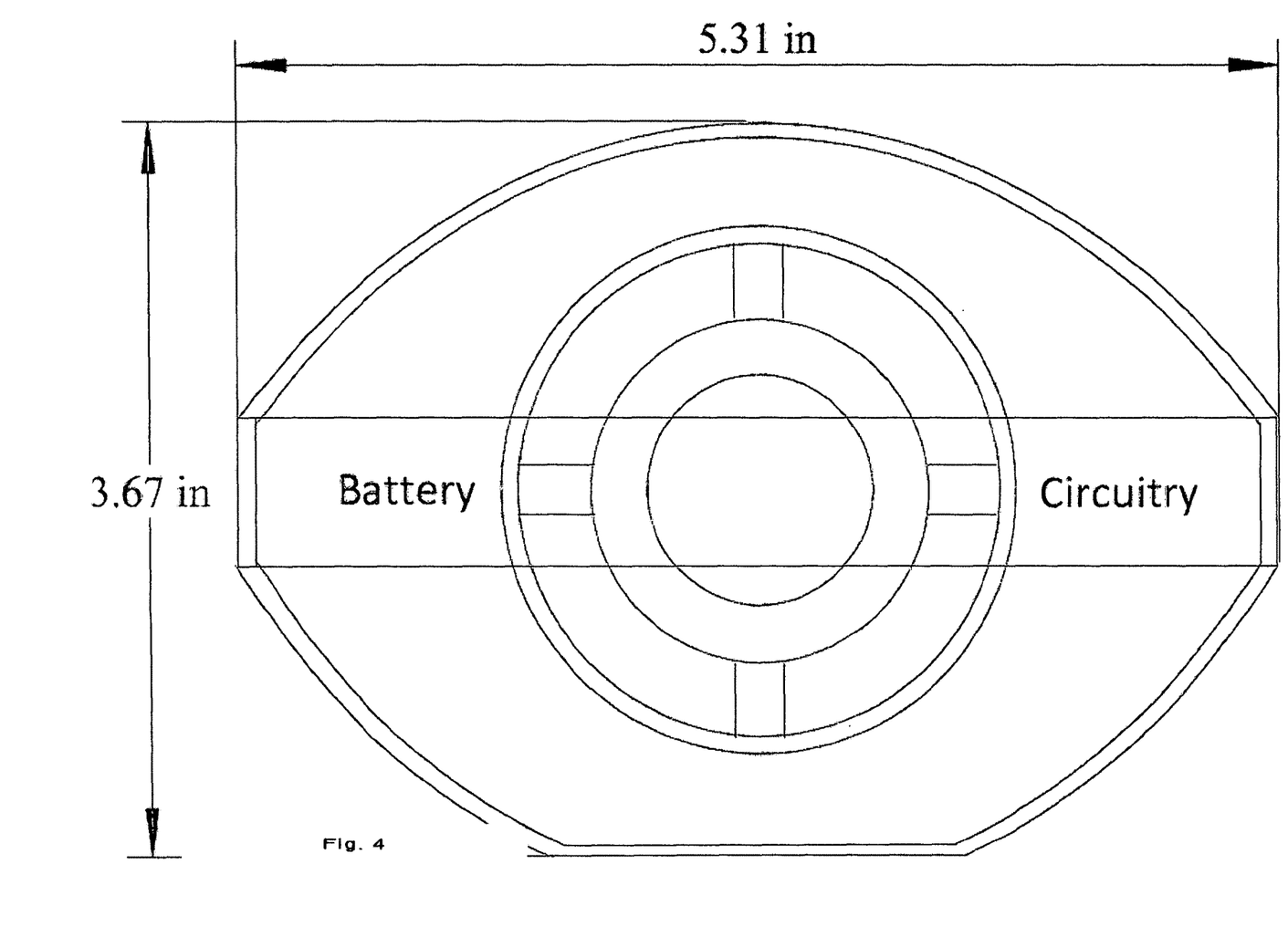

Tidal breathing is achieved by a unique double-tube system whereby the patient's normally breathing passes through a measured sized tube that routes the air around a central tube. There is a measured opening in the tube at the opposite end from the mouthpiece that creates a small amount of pressure within the tidal breathing tube, but that is hardly noticeable to the patient. The terminal resistor allows pressure to build up in the tube before releasing out of the device by series of holes hole at the end of the device with a diameter totally approximately 7.87 mm. This provides a resistance of 0.1 kPaS/L within the device. The inner tube contains the device that generates the air impulse, and this central location of the air impulse tube allows for the optimal projection of the air impulse into the patient's lungs.

Figure 1:
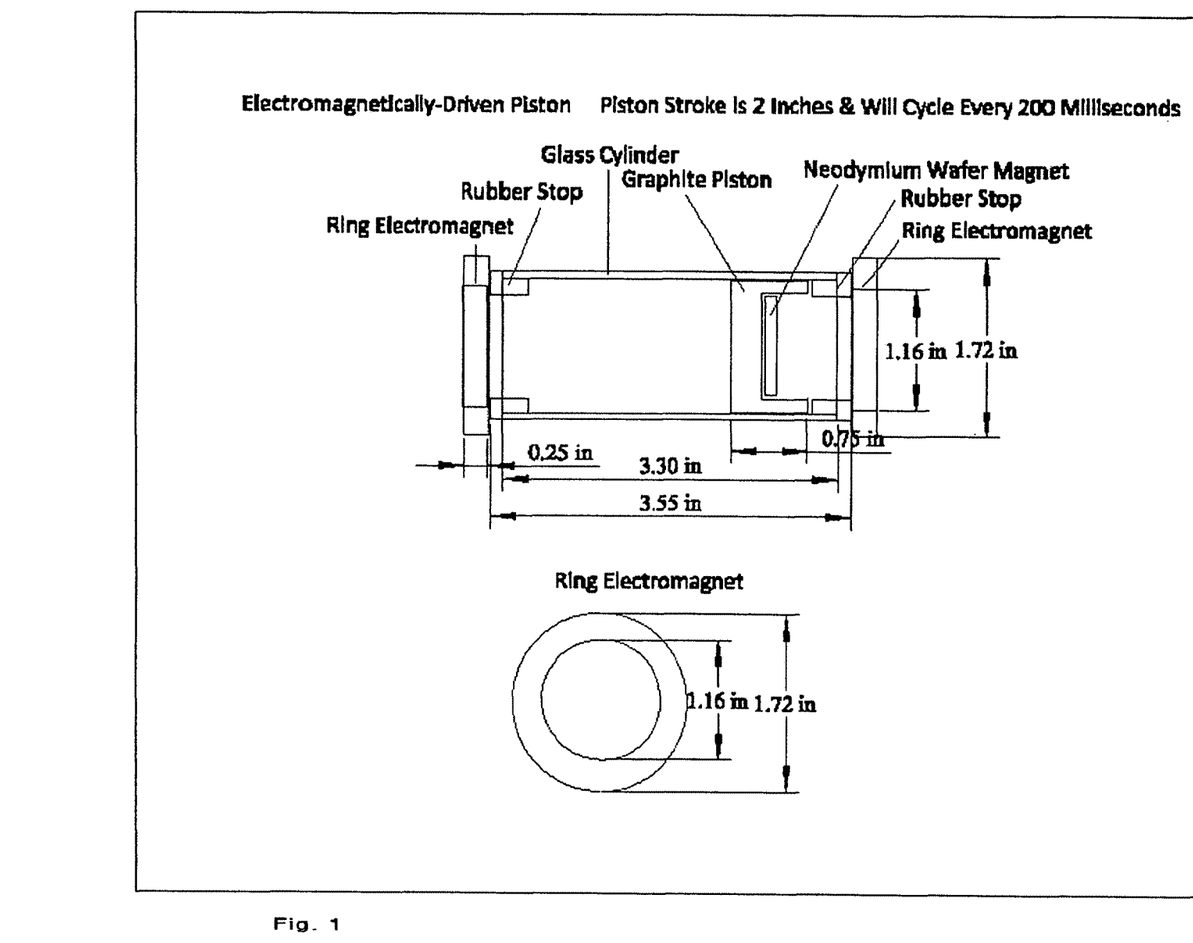

The mechanical core of the present invention is an electromagnetically-driven piston that generates measured air impulses into the lungs of the patient. The piston contains a disk-shaped neodymium permanent magnet within an indentation in piston and it's oscillations displace 40 mL of air in the cylinder in 40 ms. The piston is pushed and pulled by two ring-shaped opposite pole electromagnets. The electromagnets are located on the ends of a tube (d=1.25", L=3.5") containing the magnetically driven piston. By alternating the polarities of the electromagnets at 5 Hz, the piston is moved from one end of the cylinder to the other. The electromagnets are adjusted to the desired strength to power the piston with quick pulses to generate the necessary air impulse sent into the lungs. The current system uses N48 neodymium disk magnets (H=1/16 in D=7/8 in). The current electromagnets are 1.75" outside diameter×1.0" inside diameter×0.75" thick. The volume displacement, speed of impulse, and frequency are aligned with the current clinical impulse oscillometry system. The device is designed to work with the piston parallel to the ground, but can effectively function at a 90 degree angle. This negates the majority of gravitational effects.

Surrounding the air impulse tube and constructed within the tidal breathing tube is the pneumotachometer system that measures the differential pressures of resistance and reactance via digital pressure sensors being located on both sides of the pneumotach resistive screen. The airflow is converted into a proportional signal based on pressure differences on either side of the screen. This stainless steel 400 wire screen is a low resistive screen that ensures a linear signal for all flow rates. The wire screen has a wire diameter of 0.001 in and the resistance across the screen is between 2.34 cmH2O*s/L and 2.83 cmH2O*s/L. The digital differential pressure sensors currently connect to the device with crush-resistant silicone rubber tubing with an outer diameter of 0.25 in. The sensors are soldered to a PCB board and powered by a 5V supply voltage on the Arduino. The PCB board is connected onto the breadboard. The output of each pressure sensor is then converted into digital data and exported to analysis software. Analysis is first used to convert the data from pressure difference to flow rate by taking advantage of the linear relationship between pressure difference and laminar flow. The flow data is then compared to the raw pressure data from the backpressure sensor. The ratio of the FFT of the pressure to the FFT of the flow rate at 5 Hz is the primary output of the device.

Figure 5:
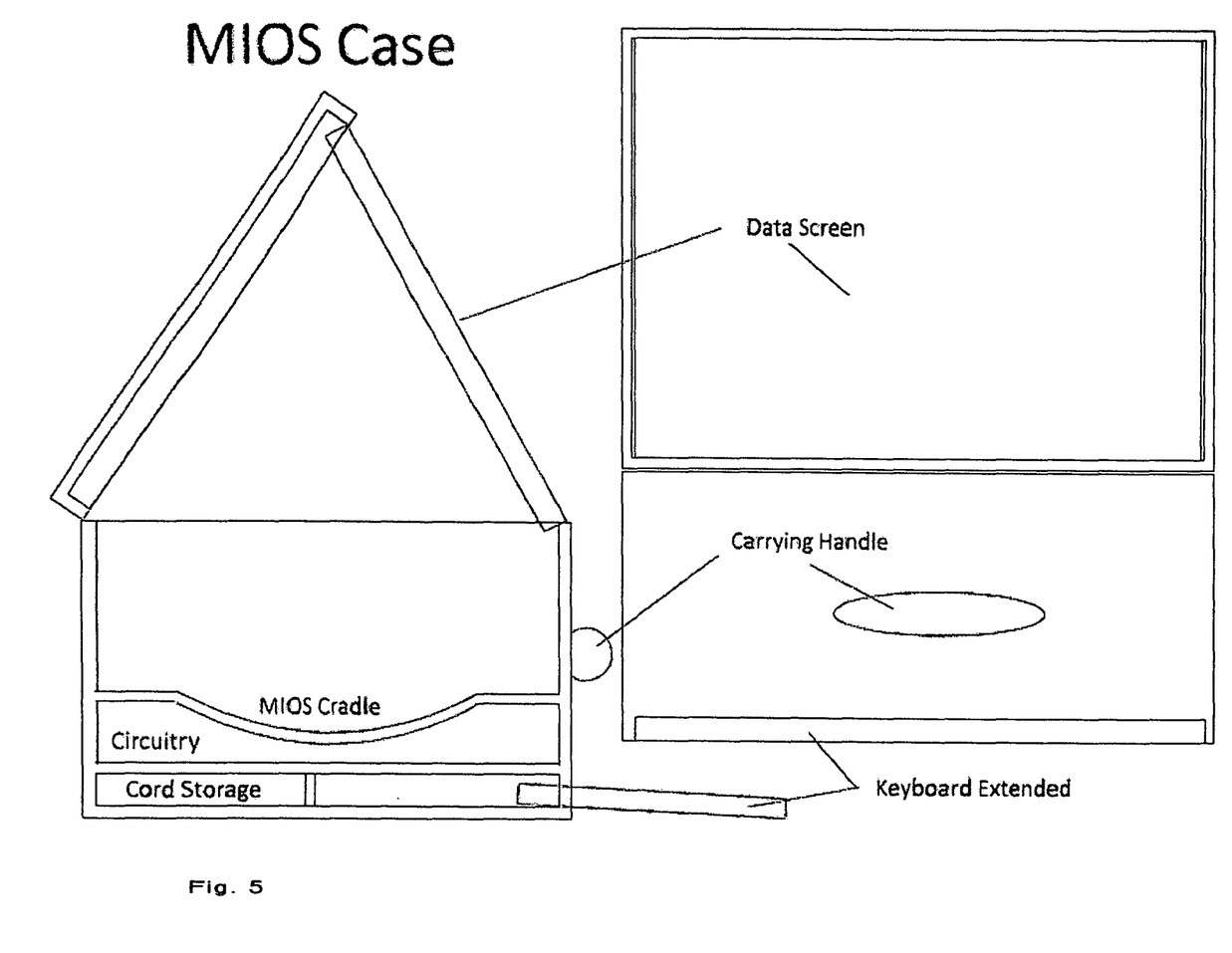

Output data is transmitted from the IOS device via Bluetooth to circuitry within the carrying case, and is then re-transmitted to a secure and encrypted cloud server where the analysis is completed. Interpreted results are transmitted back to the patient's smartphone and displayed in a manner consistent with the patient's age and preferred language. Results are also transmitted to the patient's primary care provider for storage in their electronic medical record.

Figure 6:
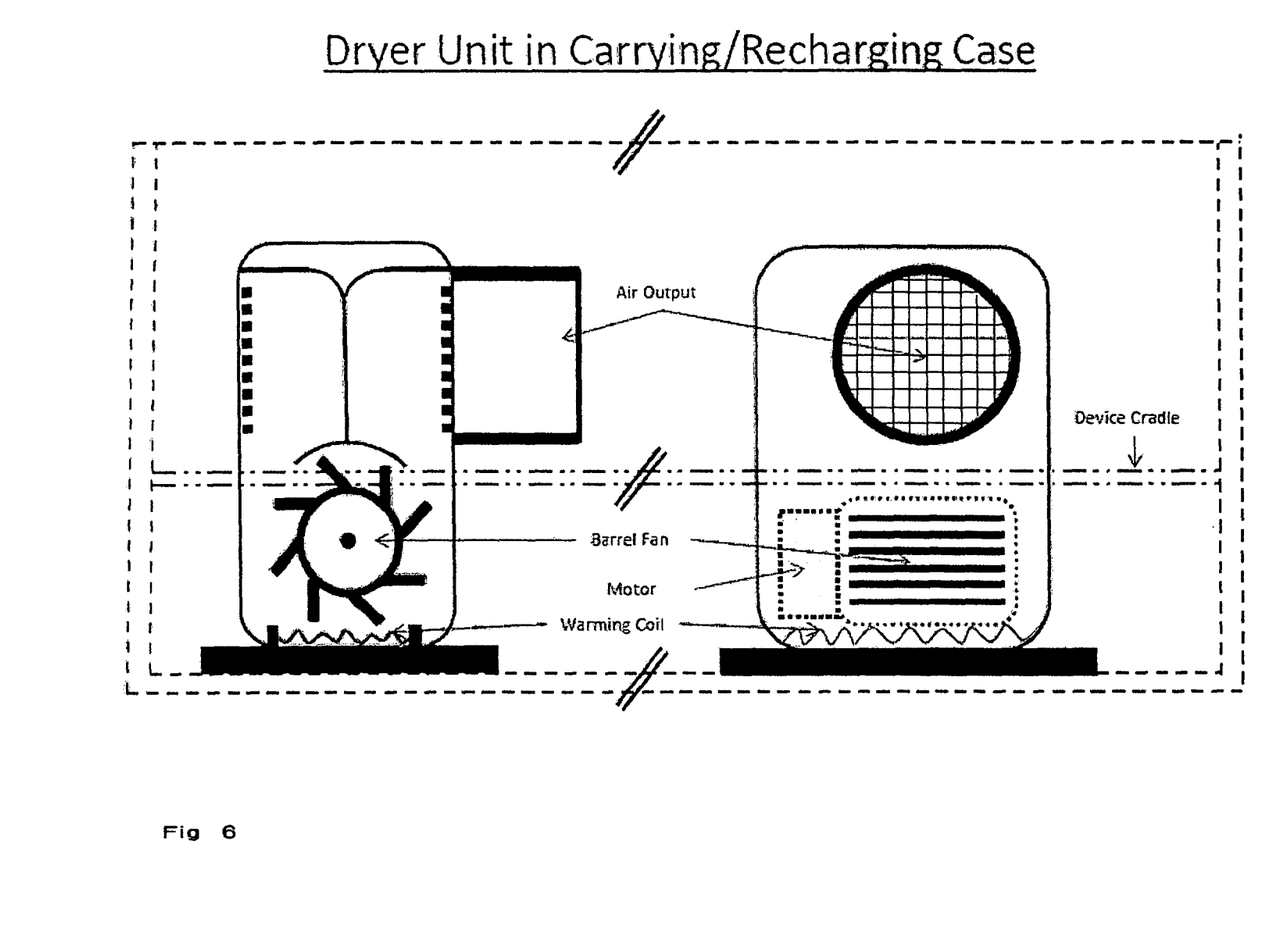

The handheld portable portion of the device is intended for the ease of use by the patient and the provider. It works in tandem with its carrying case since the carrying case houses additional circuitry, an additional battery pack, memory and communication systems, and in certain models, a data screen and pullout keyboard. This allows the IOS device itself to be as light weight and conveniently portable as possible. The IOS device has a communications range of approximately fifty yards from its carrying case. The carrying case also incorporates a dryer unit that automatically turns on and blows warmed air through the double air tubes to remove any humidity that may have accumulated during patient use. This occurs each time the IOS device is re-docked into its cradle within the carrying case.

The carrying case contains a battery pack that powers the electronics within the carrying case and also has a power cord to plug into an AC power source. The carrying case re-charges the IOS device via matching inductive magnetic units placed in the bottom of the IOS device and within the cradle of the carrying case. The IOS device is automatically recharged each time it is inserted into its docking station. The rechargeable battery pack within the IOS device is rated to last for two hours of continuous use, for four hours of intermittent use, and for twelve hours of occasional use. This provides for a high degree of portability and flexibility in how it is used.

To properly perform impulse oscillometry, the patient must utilize a nose clip to close off the nose, and hold the cheeks firmly so they do not vibrate when exposed to the air impulses of the IOS. Since the present invention is intended to be handheld and portable, allowing to patient to perform the test by them self, a unique cheek holder has been developed to fit over the mouth piece and hold the cheeks firmly, but gently, in place while the procedure is being performed. Disposable mouth pieces and disposable biofilters are supplied separately for the procedure. These must have an external diameter of 32.4 mm and be able to extend 10 mm into the front end of the device.

The invention claimed is:

1. A portable impulse oscillometer, comprising:
 a glass cylinder, where said glass cylinder comprising a double tube arrangement, wherein said double tube arrangement includes an air impulse tube and a tidal breathing tube, wherein said tidal breathing tube completely surrounds said air impulse tube;
 said glass cylinder further includes a first opening at a first end and a second opening at a second end, opposite the first end, wherein said first opening comprises a mouthpiece designed for a user's mouth to be placed on, wherein said second opening comprises an end-piece,
 said first opening is coupled to a first end of said air impulse tube for receiving projected air impulses, and is coupled to a first end of said tidal breathing tube for receiving exhalations,
 said second opening is coupled to a second end of said air impulse tube for allowing air into said air impulse tube, and is coupled to a second end of said tidal breathing tube for allowing exhalations to evacuate said tidal breathing tube;
 said air impulse tube houses an air impulse generator, said air impulse generator comprises:
 a first ring shaped electromagnet located approximately at the first end of said air impulse tube and a second ring shaped electromagnet located approximately at the second end of said air impulse tube, and
 a piston comprising a permanent magnet, wherein said piston is designed to oscillate between said first ring shaped electromagnet and said second ring shaped electromagnet, wherein said piston is electromagnetically driven to project air impulses toward said mouthpiece;
 said tidal breathing tube houses a pneumotachometer, said pneumotachometer comprises:
 one or more wire mesh screens, wherein said wire mesh screens are designed in a donut shape surrounding said air impulse tube, and
 one or more digital differential pressure sensors located adjacent to said one or more wire mesh screens;
 a printed circuit board including: control circuitry coupled to said impulse generator, processor circuitry coupled to said one or more digital differential pressure sensors, and communication circuitry capable of wireless communication; and
 a rechargeable battery coupled to said printed circuit board.

2. The portable impulse oscillometer of claim 1, wherein said piston comprises an indentation to secure said permanent magnetic.

3. The portable impulse oscillometer of clam 1, wherein said control circuitry is adapted to control a polarity of said first and second electromagnets to oscillate said piston to a desired speed.

4. The portable impulse oscillometer of claim 1, wherein said tidal breathing tube further comprises longitudinal vanes located between said first and second openings, wherein said longitudinal vanes secure said air impulse tube and equalize air pressure around the entirety of said tidal breathing tube.

5. The portable impulse oscillometer is claim 1, wherein said rechargeable battery is capable of supplying power, without being recharged, for said portable impulse oscillometer to continuously operate for two hours, or intermittently operate for six hours, or occasionally operate for a minimum of twenty-four hours.

* * * * *